United States Patent [19]

Houbion

[11] 4,397,790
[45] Aug. 9, 1983

[54] ISOPHOSPHINOLINONE DERIVATIVES

[75] Inventor: John A. Houbion, Kirkwood, Mo.

[73] Assignee: Monsanto Company, St. Louis, Mo.

[21] Appl. No.: 212,381

[22] Filed: Dec. 3, 1980

[51] Int. Cl.$^3$ .......................... C07F 9/32; A01N 57/36
[52] U.S. Cl. .................................... 260/936; 260/940; 260/941; 260/968; 260/969; 71/86
[58] Field of Search ........................................ 260/936

[56] References Cited

U.S. PATENT DOCUMENTS

| | | | |
|---|---|---|---|
| 2,944,074 | 7/1960 | Atherton | 260/943 |
| 3,239,492 | 3/1966 | Spooner | 260/936 |
| 3,931,196 | 1/1976 | Swan | 260/936 |
| 3,974,243 | 8/1976 | Kleiner | 260/941 |
| 4,110,442 | 8/1978 | Barra et al. | 260/941 |

*Primary Examiner*—Anton H. Sutto
*Attorney, Agent, or Firm*—Donald W. Peterson; Stanley M. Tarter; Gordon F. Sieckmann

[57] ABSTRACT

This invention relates to a new class of organic chemical compounds. More particularly this invention is concerned with derivatives of isophosphinolinone. Compounds of this invention may be employed as active ingredients in herbicides and/or as intermediates in the preparation of other isophosphinolinone derivatives useful to reduce herbicidal injury to treated crop plants.

2 Claims, No Drawings

ISOPHOSPHINOLINONE DERIVATIVES

This invention relates to a new class of organic chemical compounds. More particularly this invention is concerned with derivatives of isophosphinolinone. Compounds of this invention may be employed as active ingredients in herbicides and/or as intermediates in the preparation of other isophosphinolinone derivatives useful to reduce herbicidal injury to treated crop plants.

U.S. Pat. No. 3,974,243 issued to Hans-Jerg Kleiner on Aug. 10, 1976 discloses carboxyphenylalkylphosphinic acids and the esters thereof corresponding to the formula

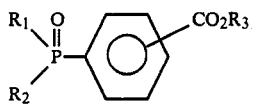

where $R_1$ is alkyl having from 1 to 4 carbon atoms, $R_2$ and $R_3$, independently, each are hydrogen, alkyl having from 1 to 12 carbon atoms, or oxyalkyl

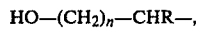

HO—(CH$_2$)$_n$—CHR—, n being 1 to 3 and R is hydrogen or alkyl having from 1 to 4 carbon atoms. A process is disclosed for the preparation of these compounds.

The aforementioned compounds are said to be useful as intermediate products in the manufacturing of plant protecting agents and pharmaceuticals.

The compounds of the present invention are represented by the formula

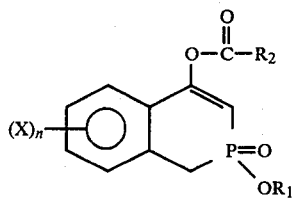

wherein

X is independently selected from the group consisting of halogen, hydroxy, alkyl having 1 to 4 carbon atoms, alkoxy having 1 to 4 carbon atoms, nitro cyano and $CF_3$, n is an integer from 1 to 4, $R_1$ is alkyl having 1 to 4 carbon atoms, $R_2$ is selected from the group consisting of alkenyl having 1 to 4 carbon atoms, haloalkyl having 1 to 4 carbon atoms,

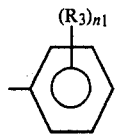

wherein $R_3$ is independently selected from the group consisting of alkyl having 1 to 4 carbon atoms, $CF_3$, fluorine, chlorine, bromine, iodine, alkoxy having 1 to 4 carbon atoms, nitro and wherein $n_1$ is an integer from 1 to 5. X, n, $R_1$, $R_2$, $R_3$, and $n_1$, are selected totally independent of each other.

Illustrative halogens represented by X include iodine, chlorine, fluorine and bromine although chlorine is the preferred halogen group.

Illustrative linear and branched alkyl groups represented by X include methyl, ethyl, propyl and butyl.

Illustrative alkoxy groups represented by X include methoxy, ethoxy, proproxy and butoxy.

Illustrative linear and branched alkyl groups represented by $R_1$ include methyl, ethyl, propyl, butyl although ethyl is a preferred group for $R_1$.

Illustrative alkenyl groups represented by $R_2$ include ethylene, propylene, butylene and the like.

Illustrative haloalkyl groups represented by $R_2$ include chloromethyl, chloroethyl, chloropropyl, chlorobutyl and the like, iodomethyl, iodoethyl, iodopropyl, iodobutyl and the like, bromoethyl, bromomethyl, bromopropyl, bromobutyl and the like, although chloroethyl is a preferred haloalkyl group.

Illustrative alkyl groups represented by $R_3$ include methyl, ethyl, propyl, butyl although methyl is a preferred alkyl group for $R_3$.

Also n is preferably 1 and $n_1$ is preferably 1. When X is chlorine and n is 1, the 8 position is preferred. When $R_3$ is methyl and $n_1$ is 1, the ortho position is preferred.

In accordance with the present invention, compounds of the formula (I) are prepared by reacting a compound of the formula

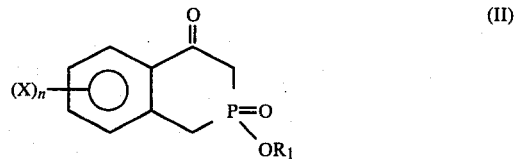

wherein $R_1$ is as defined above, with a compound of the formula

R$_2$COCl          (III)

where $R_2$ is as defined above, in the presence of a hydrogen chloride scavanger.

Typical hydrogen chloride scavangers include tertiary amines such as pyridine, lutidine, DBU and triethylamine. Triethylamine is preferred as hydrogen chloride scavanger.

Typically, compounds of formula (III) are known as acid chlorides.

The aforedescribed reaction is carried out at a temperature in the range from about 0° to about 100° and preferably from about 10° to about 90° C., although greater or lesser temperatures may be employed if desired.

The molar ratio of the compounds of formula (II) to the compounds of formula (III) is in the range from about 2:1 to about 1:2 and preferably from about 1.5:1 to about 1:1.5 although greater or lesser molar ratios may be employed if desired.

Compounds of formula (II) are useful as intermediates in the preparation of compounds of formula (I).

In further accordance with the present invention, compounds of formula (II) are prepared by reacting a compound of the formula

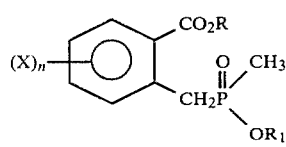

wherein R is a branched or linear alkyl of the formula $(CH_2)_{n_2}CH_3$. $n_2$ is an integer from 0 to 3 and wherein X, n, and $R_1$ are as previously defined, with an aprotic base selected from the group consisting of potassium alkoxide, potassium tert-butoxide being preferred, sodium alkoxide, sodium hydride, potassium hydride, lithium hydride, combinations thereof and the like and metal amides such as sodium, lithium or potassium amide in the presence of at least one inert anhydrous solvent.

Typical alkyl radicals represented by R include methyl, ethyl, propyl and butyl.

Preferably $n_2$ is 0 or 1 and preferably R is methyl or ethyl.

Potassium t-butoxide is preferred as an aprotic base.

Typical inert anhydrous solvents include ethers such as diethylether, dibutylether and dimethoxyethane, and hydrocarbons such as benzene, toluene although diethylether is preferred as an inert anhydrous solvent.

The aforedescribed reaction is carried out at a temperature in the range from about 0° to about reflux temperature of the inert anhydrous solvent and preferably from about 10° to about 75° C., although greater or lesser temperatures may be employed if desired.

The weight ratio of aprotic base to compounds of formula (IV) is in the range from about 2:1 to about 1:2 and preferably from about 1.5:1 to about 1:1.5 although greater or lesser weight ratios may be employed if desired.

In further accordance with the process of this invention, compounds of formula (IV) are prepared by reacting a compound of the formula

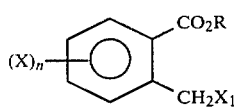

wherein $X_1$ is bromine, chlorine, iodine, wherein R, $R_1$, X, and n are as previously defined, with a dialkylmethylphosphonite of the formula $(R_1O)_2PCH_3$     (VI)

wherein $R_1$ is as previously defined.

The aforedescribed reaction is carried out at a temperature in the range from about 0° to about 180° C. and preferably from about 20° C. to about 150° C., although greater or lesser temperatures may be employed if desired. If an inert solvent is used, toluene or xylene are preferred.

The molar ratio of the compounds of formula (VI) to the compound of formula (VI) is in the range from about 2:1 to about 1:2 and is preferably from about 1.5:1 to about 1:1.5 although greater or lesser molar ratios may be employed.

In another embodiment of this invention, compounds of the formula

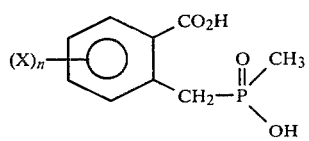

are prepared by the acid hydrolysis of a compound of the formula

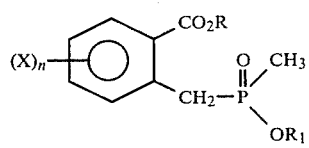

wherein R, X, n and $R_1$ are as previously defined, although R and $R_1$ are preferentially ethyl, X is preferably chlorine and n is preferably 1, with chlorine in the 3-position.

The hydrolysis are peformed in an aqueous inorganic acid such as hydrochloric or hydrobromic acid with or without a water soluble solvent such as alcohol, tetrahydrofuran, dimethoxyethane or dioxane at a temperature in the range from about 20° to reflux temperature with about 80° to about 100° C. being a preferred temperature range.

The following examples are presented to define the process of this invention more fully without any intention of being limited thereby. All parts and percentages are by weight unless indicated otherwise.

Part A of Example 1 illustrates preparation by a method known to those skilled in the art of a starting reactant exemplary of compounds of formula (V).

Part B of Example 1 relates to subsequent preparation of species representative of compounds (IV), (II), and (I) according to the process of this invention.

EXAMPLE 1

PART A: PREPARATION OF 2-BROMOMETHYL-3-CHLOROETHYL-BENZOATE

A mixture of 34 g. (0.2 mol) of 2-methyl-3-chlorobenzoic acid and 50 mL. of commercially available triethylorthoformate was refluxed for 6 hours, upon which bulb-to-bulb distillation gave 35.5 g. (89% yield) of ethyl-3-chloro-2-methylbenzoate as a clear liquid having a boiling point of 80° C. at a pressure of 0.1 mmHg.

Anal. Calculated: C, 60.46; H, 5.58. Found: C, 60.50; H, 5.62.

A 500 mL. flask was charged with 33.3 g. (0.167 mol) of ethyl 3-chloro-2-methylbenzoate prepared as described above and 200 mL. of carbon tetrachloride. While maintaining the reflux by means of a 275 watt sunlamp clamped underneath the flask, 28.4 g. (0.177 mol) of molecular bromine in 50 mL. of carbon tetrachloride was slowly introduced below the surface. Reflux was continued for 10 minutes and the solvent was then evaporated to give 45.2 g. (92% yield) of 2-bromomethyl-3-chloroethylbenzoate as a crude product representative of reactant compounds of formula (V).

Anal. Calculated: C, 43.27; H, 3.63. Found: C, 42.76; H, 3.58.

PART B: REACTION STEPS OF THE PROCESS OF THIS INVENTION

Step A

A mixture of 22.7 g. (82 mmmol.) of the 2-bromomethyl-3-chloroethylbenzoate prepared as described in Part A above and 12.5 g. (90 mmol.) of commercially available diethylmethyl phosphonite in 120 mL. of toluene was heated until evolution of ethyl bromide ceased. Evaporation of the solvent and Kugelrhor distillation gave 24 g. (96% yield) of ethyl ester of 3-chloro-2-[(ethoxymethylphosphinyl)methyl]benzoic acid having a boiling point of 136° C. at a pressure of 0.1 mm Hg as a representative species of compounds of formula (IV).

Anal. Calc'd. for $C_{13}H_{18}ClO_4P$: C, 51.24; H, 5.95; Cl, 11.63. Found: C, 51.14; H, 5.99; Cl, 11.56.

Step B

To a rapidly stirred suspension of 16 g. (140 mmol.) of potassium t-butoxide in 600 mL. of anhydrous ether was added dropwise under nitrogen 11.7 g. (35 mmol.) of ethyl ester of 3-chloro-2-[(ethoxymethylphosphinyl)methyl]benzoic acid previously prepared as in Step A of Part B above in 50 mL. of ether. The reaction mixture was stirred for an additional 30 minutes. 100 mL. of water was added followed by concentrated hydrochloric acid to provide a pH of 7. The ether layer was separated, washed with brine and concentrated. Crystallization from hexane/methylene chloride gave 7.5 g. (83% yield) of 8-chloro-2-ethoxy-2,3-dihydro-2-oxo-4(1H)-isophosphinolinone as a representative species of compounds of formula (II).

Anal. Calculated: C, 51.08; H, 4.68; Cl, 13.71. Found: C, 51.11; H, 4.68; Cl, 13.68.

Step C

A solution of 1.2 g (12 mmol.) of triethylamine in 50 mL of methylene chloride was added dropwise at 20° C. to a mixture of 2.8 g (10.8 mmol.) of 8-chloro-2-ethoxy-2,3-dihydro-2-oxo-4(1H)isophosphinolinone prepared as described in Step B, Part B of Example 1 representative of compounds of formula (II) and 1.7 g (11 mmol.) of o-toluylchloride. After 30 minutes at reflux temperature, the organic solution was washed with diluted acid, with saturated sodium bicarbonate and was concentrated. Crystallization from methylcyclohexane gave the desired product P-oxo-(8-chloro-1,2-dihydro-2-ethoxy-4-isophosphinolinyl)-2-methylbenzoate, mp 165°-6° (3.3 g, 81% yield) as a species of compound of formula (I).

Anal. Calculated for $C_{19}H_{18}ClO_4P$: C, 60.57; H, 4.82; P, 8.22. Found: C, 60.63; H, 4.83; P, 8.32.

EXAMPLE 2

10.4 grams (0.34 moles) of the ethyl ester of 3-chloro-2-[(ethoxymethylphosphinyl)methyl]-benzoic acid prepared as described in Part B Step A of Example 1 was admixed with 20 ml of concentrated hydrochloric acid and 80 ml of dioxane. The resulting composition was saturated with hydrochloric acid (gas) and refluxed for 12 hours. The composition was concentrated, extracted with ether and the ether solution was dried over magnesium sulfate. The ether was evaporated and the residue was recrystallized from acetone/$CH_2Cl_2$ to give 7.5 grams (89% yield) of 3-chloro-2-[(hydroxymethylphosphinyl)methyl]-benzoic acid having a melting point of 219°-220° C.

Anal. Calculated: C, 43.48; H, 4.05; Cl, 14.26. Found: C, 43.26; H, 4.11; Cl, 14.19.

In addition to being useful as an intermediate compound to prepare compounds of formula (II) and (I) as previously described, the ethyl ester of 3-chloro-2-[(ethoxymethyl-phosphinyl)methyl]-benzoic acid has been found effective as a post-emergent herbicide.

The post-emergence herbicidal activity of ethyl ester of 3-chloro-2[(ethoxymethylphosphinyl)methyl]-benzoic acid of this invention is demonstrated by testing of the following Example 3.

EXAMPLE 3

A good grade of top soil was placed in aluminum pans having holes in the bottom and compacted to a depth of 0.95 to 1.27 cm. from the top of the pan. A predetermined number of seeds of each of several dicotyledonous and monocotyledonous annual plant species and vegetative propagules for the perennial plant species were placed on the soil and pressed into the soil surface. The seeds and vegatative propagules were covered with soil and leveled. The pans were then placed on a sand bench in the greenhouse and watered from below as needed. After the plants reached the desired age of two weeks, each pan except for the control pans was removed individually to a spraying chamber and sprayed by means of an atomizer operating at a positive air pressure of approximately 1.46 kg/$cm^2$ absolute. The atomizer contained 6 ml. of a solution or suspension of ethyl ester of 3-chloro-2[(ethoxymethylphosphinyl)methyl]-benzoic acid. In that 6 ml., was an amount of a cyclohexanone emulsifying agent mixture to give a spray solution or suspension which contained about 0.4% by weight of the emulsifier. The spray solution or suspension contained a sufficient amount of the ethyl ester of 3-chloro-2[(ethoxymethylphosphinyl)methyl]-benzoic acid in order to give application rates corresponding to those set forth in the tables. The spray solution was prepared by taking an aliquot of a 1.0% by weight stock solution or suspension of the candidate chemical in an organic solvent such as acetone or tetrahydrofuran or in water. The emulsifying agent employed was a mixture comprising 35 weight percent butylamine dodecylbenzene sulfonate and 65 weight percent of a tall oil ethylene oxide condensate having about 11 moles of ethylene oxide per mole of tall oil. The pans were returned to the greenhouse and watered as before and the injury to the plants as compared to the control was observed at approximately two and four weeks as indicated in the tables under WAT and the results recorded.

The post-emergence herbicidal activity index employed in Table I is as follows:

| Plant Response | Index |
| --- | --- |
| 0-24% control | 0 |
| 25-49% control | 1 |
| 50-74% control | 2 |
| 75-99% control | 3 |
| 100% control | 4 |

The plant species utilized in these tests are identified by letter in accordance with the following legend:
A—Canada Thistle*
B—Cocklebur
C—Velvetleaf
D—Morningglory E—Lambsquarters
F—Smartweed
G—Yellow Nutsedge*
H—Quackgrass*
I—Johnsongrass*
J—Downy Brome
K—Barnyardgrass

*—established from vegetative propagules.

TABLE I

| WAT | kg/h | A | B | C | D | E | F | G | H | I | J | K |
|---|---|---|---|---|---|---|---|---|---|---|---|---|
| 2 | 11.2 | 1 | 2 | 0 | 2 | 2 | 2 | 0 | 0 | 0 | 0 | 1 |

Herbicidal compositions, including concentrates which require dilution prior to application to the plants, of this invention contain from about 5 to about 95 parts by weight of at least one compound of this invention and from about 5 to about 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from about 5 to about 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecyl-mono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific compound employed. In foliar treatment for the control of vegetative growth, the active ingredients are applied in amounts from about 0.112 to about 56.0 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

This invention further relates to the safening of crop plants and to the use of herbicides utilizing a safening agent or composition containing a safening agent to reduce the herbicidal injury to treated crop plants. More specifically, the invention is concerned with methods of treating a seed bed prior to seeding with compounds of the formula (I)

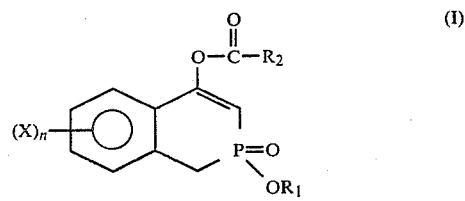

wherein
X is independently selected from the group consisting of bromine, chlorine, iodine, fluorine, hydroxy, alkyl having 1 to 4 carbon atoms, alkoxy having 1 to 4 carbon atoms, nitro cyano and $CF_3$, n is an integer from 1 to 4, $R_1$ is selected from the group consisting of alkyl having 1 to 4 carbon atoms, $R_2$ is selected from the group consisting of alkenyl having 1 to 4 carbon atoms, haloalkyl having 1 to 4 carbon atoms or,

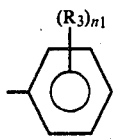

wherein $R_3$ is independently selected from the group consisting of alkyl having 1 to 4 carbon atoms, $CF_3$, fluorine, chlorine, bromine, iodine and alkoxy having 1 to 4 carbon atoms, nitro and wherein $n_1$ is an integer from 1 to 5, and X, n, $R_2$, $R_3$, n, are selected independent of each other, or compositions containing compounds of formula (I) in order to prevent or reduce the injury to the crop plant which would otherwise occur due to the use of an alpha-haloacetanilide or carbamate herbicide alone. This invention is also concerned with novel compositions which comprise an acetanilide or carbamate herbicide and a compound of formula (I).

In practice it has been found that acetanilide and carbamate herbicides are effective in controlling certain weeds in the presence of growing crops. It has been found that when acetanilide or carbamate herbicides are applied at rate necessary to stunt or kill the weeds, many of these herbicides injure certain crop plants thus slowing growth and development. This injury results in decreased crop yields, thereby reducing the effectiveness of certain herbicides in controlling weeds in the presence of crops. Obviously, a safening agent or composition thereof, that could be used to treat the crop plant locus, resulting in a reduction of injury due to application of the herbicide without a corresponding reduction of herbicidal action on the weed, is quite beneficial.

In accordance with the novel aspects of the present invention, crop plants are protected and the tolerance of said crop plants is increased to minimize injury due to the application thereto of an acetanilide herbicide, without a corresponding significant reduction in injury to the weeds by treating seed bed before seeding with an effective amount of a safening agent comprising a compound having the formula

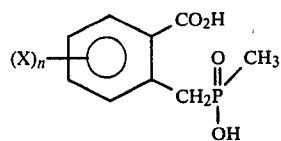

where X and n are as previously described.

Classes of acetanilide herbicides employed as aforedescribed in the compositions and methods of this invention include herbicides having as active ingredients acetanilides and carbamates.

Typical acetanilide based herbicides include these herbicides having as an active ingredient 2-chloro-2',6'-diethyl-N-(methoxymethyl) acetanilide, 2-chloro-2'6'-diethyl-N-(butoxymethyl) acetanilide, and the like. The preparation and use of 2-chloro-2',6'-diethyl-N-(methoxymethyl) acetanilide and 2-chloro-2',6'-diethyl-N-(butyoxymethyl) acetanilide to control the growth of undesired plants is described in U.S. Pat. No. 3,442,945 issued to John F. Olin on May 6, 1969. Herbicidal compositions containing these compounds are disclosed in U.S. Pat. No. 3,547,620 issued to John F. Olin on Dec. 15, 1970. Typical carbamate herbicides include those herbicides having S-(2,3,3 trichlororoallyl) diisopropylthiocarbamate) as an active ingredient and sold under the registered trademark Avadex ® by the Monsanto Company.

Although it is known that a wide variety of acetanilides are useful as selective herbicides, it is evident from the prior art that alpha-haloacetanilides are commercially significant. Because of the wide usage of alpha-halo-acetanilides, these herbicides are the preferred herbicides for safening by the methods and compositions of the present invention. Nevertheless, the present safening methods and compositions are useful for safening the herbicidal acetanilide family of compounds and the instant invention is not limited to only alpha-haloacetanilide herbicides.

Treatment of the seed bed refers to the application of the herbicide and safening agent, in admixture or in sequence, to the seed bed.

The safening agents of this invention may be applied in a mixture with the above-named herbicides, or the components of the mixture can be used sequentially. In the case of a sequential treatment, the safening agent maybe applied either before or after application of the herbicide. Effective herbicidal amounts of the particular herbicide employed are well understood by those skilled in the art, and such amounts are used together with an effective safening amount of a compound of formula (I). The term "effective safening amount" refers to the amount of safening agent required to effectively reduce the crop injury caused by application of a herbicide at a given rate. The amount of safening agent employed in the method and compositions of this invention will vary depending upon the particular herbicide with which the safening agent is employed, the rate of application of the herbicide, the crop to be protected as well as the manner of application of the safening agent. The ratio of herbicide to safening agent may vary depending upon the age of the plants at time of treatment, climatic conditions, soil, etc. It is generally preferred to employ a weight ratio of herbicide to safening agent ranging from about 1:4 to about 8:1.

In each test a crop plant, with or without weeds, is grown in a container, and there is an application of the herbicide and a safening agent. In each test there is also a container which receives no application at all, a container to which only the herbicide is applied, and a container to which only the safening agent is applied. The untreated container shows normal plant growth as standard, and it also serves as an indicator of extraneous conditions which may affect the plants. the other containers show the effect of the herbicide alone, the effect of the safening agent alone, and the effect of the application of both. These effects are in terms of percent inhibition of plant growth relative to the plants in the untreated container.

The "safening effect" is calculated by adding the percent inhibition observed when the herbicide is applied alone to the percent inhibition observed when the safening agent is applied alone (in no instance, however, will this sum be taken as greater than 100), then subtracting from that sum the percent inhibition observed when the herbicide and safening agent are both applied. The percent inhibition as used hereinafter refers to the percent injury of weeds or crop plants. Complete inhibition or kill is 100%.

The effectiveness of species of compound of formula (I) for the purposes of this invention is demonstrated by the results obtained using the various test procedures afore and hereinafter described. Specific individual compounds employed as safening agents in these procedures are identified. The herbicide as used in the test procedures was in the form of a formulation comprising the named active ingredient, a solvent and an emulsifier. All rates of application of the herbicide and safening agent in the following examples are shown in kilograms per hectare unless otherwise noted. In those tests where the procedures are replicated, the results represent an average of all replicates. The compounds as employed in the following examples serve only to illustrate the novel aspects of the invention and should not be construed as a limitation on its scope.

EXAMPLE 4

A good grade of top soil was placed in a container and compacted to a depth of approximately 1.27 cm. from the top of said container. A predetermined number of seeds of each of the crop species to be tested were placed on top of the soil. A quantity of soil sufficient to substantially fill the container was measured and placed in a second container. A measured quantity of the safening agent dispersed or dissolved in a suitable carrier was applied to the soil in the second container. A measured quantity of formulated 2-chloro-2',6'-diethyl-N-(methoxymethyl)acetanilide dispersed or dissolved in a suitable carrier was then sprayed on the soil previously treated with the safening agent. The soil containing the safening agent and herbicide was thoroughly mixed. This mixing is referred to as incorporation of the herbicide and safening agent into the soil. The incorporation provides a substantially uniform distribution of the safening agent and herbicide throughout the soil. The seeds were covered with the soil containing the safening agent and herbicide and the pots were leveled. The pots were then placed on a sand bench in the greenhouse and watered from below as needed. The plants were observed at the end of approximately 21 days and the results in terms of percent inhibition of each seed lot were recorded.

The test results summarized in Table II illustrate the reduction in the inhibition of crop plants which was achieved employing the aforedescribed seed bed incorporation of herbicide and safening agent into the seed bed prior to seeding when 2-chloro-2',6'-diethyl-N-(methoxymethyl)acetanilide was employed as the active ingredient in a herbicide in conjunction with two species of safening agent of this invention.

TABLE II

| Safening Agent No. | Herbicide Rate, lbs/acre | Safening Agent Rate, lb/acre | Safening Effect | | |
|---|---|---|---|---|---|
| | | | Green Fox Tail | Sorghum | Wheat |
| 1 | 0.5 | 8.0 | X | 50 | 25 |
| 1 | 1.0 | 8.0 | X | 45 | 20 |
| 1 | 2.0 | 8.0 | X | 60 | XX |
| 1 | 4.0 | 8.0 | X | 60 | XX |
| 2 | 0.5 | 8.0 | X | 50 | XX |
| 2 | 1.0 | 8.0 | X | 40 | XX |
| 2 | 2.0 | 8.0 | X | 40 | XX |
| 2 | 4.0 | 8.0 | X | 30 | XX |

Wherein the Safening Agent No. 1 is P-oxo-(8-chloro-1,2-dihydro-2-ethoxy-4-isophosphinolyl)-2-methylbenzoate and Safening Agent No. 2 is 3-chloro-2-[(ethoxymethylphosphinyl)methyl]glycinate.

X indicates an insignificant safening effect of 0±19 on green fox tail (actually here 0±5) as a species of grass and XX indicates an insignificant safening effect of 0±19 on or wheat as a species of crops.

Table III illustrates the effective use of P-oxo-(8-chloro-1,2-dihydro-2-ethoxy-4-isophosphinyl)-2-methylbenzoate of this invention as a safening agent in a preseeding seed bed incorporation with the active ingredients of three herbicides (2, 3 and 4) as identified below on sorghum as a species of crop.

TABLE III

| Herbicide Rate, lbs/acre | Herbicide No. | Safening Agent Rate, lb/acre | Safening Effect Sorghum |
|---|---|---|---|
| 0.5 | 1 | 8.0 | 50 |
| 1.0 | 2 | 8.0 | 28 |
| 2.0 | 3 | 8.0 | 20 |

The active ingredient of Herbicide No. 1 is S-(2,3,3trichloroallyl)diisopropylthiocarbamate, the active ingredient of Herbicide No. 2 is 2chloro-2',6'diethyl-N-(methoxy-methyl)acetanilide, and the active ingredient of Herbicide No. 3 is 2chloro-2,6'diethyl-N-(butoxymethyl)acetanilide.

All of the tests within the above example were not necessarily conducted at the same time. It should also be understood, that an untreated container, plus containers with the herbicide alone and the safening agent alone, are employed for each test initiation date as controls to obtain the herbicide and safening effect data for tests begun on that particular date.

The herbicide, safening agent or mixture thereof may be applied to the seed bed alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water a wetting agent, dispersing agent, or emulsifying agent any suitable combination of these.

When applying the herbicide, safening agent or mixture thereof to the seed bed useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No.

2,547,724 issued to Norman K. Sundholm on Apr. 3, 1951, columns 3 an 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixture thereof in a liquid or particulate solid form can be carried out by conventional techniques utilizing, for example, spreaders, power dusters, boom and hand sprayers, spray dusters and granular applications. The compositions can also be applied from airplanes as a dust or spray. If desired, application of the compositions of the invention to plants can be accomplished by incorporating the compositions in the soil or other media.

There are thus also provided by this invention novel seed treating compositions containing one or more of the described active safening agents intimately dispersed in an inert carrier or diluent for the intended use in seed bed incorporation.. Such carriers may be either solids, such as talc, clay, diatomaceous earth, sawdust, calcium carbonate, and the like or liquids such as water, kerosene, acetone, benzene, toluene, xylene, and the like in which the active agent may be either dissolved or dispersed. Emulsifying agents are advisably used to achieve a suitable emulsion if two immiscible liquids are used as a carrier. Wetting agents may also be used to aid in dispersing the active safening agent in liquids used as a carrier in which the agent is not completely soluble. Emulsifying agents and wetting agents are sold under numerous tradenames and may be either pure compounds, mixtures of compounds of the same general groups, or they may be mixtures of compounds of different classes. Typical satisfactory surface-active agents which may be used are alkali metal, higher alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8–18 carbon atoms, long chain quaternary ammonium compounds, sodium salts of petroleum-derived alkylammonium compounds, sodium salts of petroleum-derived alkylammonium compounds, sodium salts of petroleum-derived alkylsulfonic acids, polyethylene sorbitan monooleate, alkylaryl polyether alcohols, water-soluble lignin sulfonate salts, alkali-case in compositions, long chain alcohols usually containing 10–18 carbon atoms, and condensation products of ethylene oxide with fatty acids, alkylphenols and mercaptans.

Although this invention has been described with respect to specific embodiments and modifications, the details thereof are not to be construed as limitations, for it will be apparent that various equivalents, changes and modifications may be resorted to without departing from the spirit and scope thereof and it is understood that such equivalent embodiments are intended to be included herein.

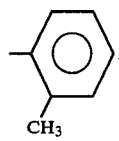

What is claimed is:
1. A compound of the formula

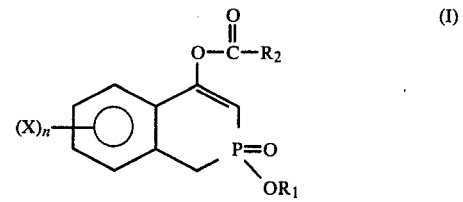

wherein
X is independently selected from the group consisting of bromine, chlorine, iodine, fluorine, hydroxy, linear alkyl having 1 to 4 carbon atoms, linear alkoxy having 1 to 4 carbon atoms, nitro, cyano and $CF_3$,
n is an integer from 1 to 4,
$R_1$ is alkyl having 1 to 4 carbon atoms,
$R_2$ is selected from the group consisting of alkenyl having 1 to 4 carbon atoms, haloalkyl having 1 to 4 carbon atoms,

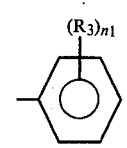

wherein $R_3$ is independently selected from the group consisting of linear alkyl having 1 to 4 carbon atoms, $CF_3$, fluorine, chlorine, bromine, iodine and linear alkoxy having 1 to 4 carbon atoms, nitro and wherein $n_1$ is an integer from 1 to 5.

2. A compound of claim 1, wherein X is chlorine in the 8-position, n is 1, $R_1$ is ethyl, and $R_2$ is